United States Patent
Moss et al.

(10) Patent No.: US 6,429,015 B1
(45) Date of Patent: Aug. 6, 2002

(54) METHOD FOR IDENTIFYING ACTIVE SUBSTANCES

(75) Inventors: David Moss, Waldbronn; Herbert Platsch, Darmstadt; Kathrin Füchsle; Ralf Masuch, both of Karlsruhe, all of (DE)

(73) Assignees: Forschungszentrum Karlsruhe GmbH, Karlsruhe; BASF AG, Ludwigshafen, both of (DE)

(*) Notice: Subject to any disclaimer, the term of this patent is extended or adjusted under 35 U.S.C. 154(b) by 0 days.

(21) Appl. No.: 09/508,416
(22) PCT Filed: Aug. 21, 1998
(86) PCT No.: PCT/EP98/05328
§ 371 (c)(1),
(2), (4) Date: May 22, 2000
(87) PCT Pub. No.: WO99/12017
PCT Pub. Date: Mar. 11, 1999

(30) Foreign Application Priority Data

Sep. 4, 1997 (DE) .......................... 197 38 566

(51) Int. Cl.[7] .............................................. G01N 21/35
(52) U.S. Cl. ......................... 436/34; 436/86; 436/94; 436/171
(58) Field of Search .................. 436/34, 35, 164, 436/171, 86, 94; 422/82.05, 82.09; 250/339.08, 339.12

(56) References Cited

U.S. PATENT DOCUMENTS

| | | | | |
|---|---|---|---|---|
| 4,472,505 A | * | 9/1984 | Manabe et al. | 436/47 |
| 4,722,830 A | * | 2/1988 | Urie et al. | 422/62 |
| 5,339,255 A | | 8/1994 | Suzuki et al. | |
| 5,519,220 A | * | 5/1996 | Truett | 250/339.08 |
| 5,677,191 A | * | 10/1997 | Truett | 436/166 |
| 6,054,711 A | * | 4/2000 | Bruening et al. | 250/339.08 |

FOREIGN PATENT DOCUMENTS

| | | |
|---|---|---|
| WO | WO 85/04478 | 10/1985 |
| WO | WO 96/18096 | 6/1996 |

\* cited by examiner

*Primary Examiner*—Jeffrey Snay
(74) *Attorney, Agent, or Firm*—Venable; Robert Kinberg

(57) ABSTRACT

The invention relates to a method and a device for identifying active substances in order to determine the formation of complexes between reactants. According to the inventive method, at least two reactants are mixed and made to react to form a complex. The infrared spectrum of the individual reactants which have not yet been reacted in the mixture is measured during a first time interval and at least a second infrared measurement is conducted to measure the complex formed by the reactants during a second interval. The difference between the two spectra measured during different moments is then determined. The reactants whose differential spectrum exhibits a band structure are selected as active substances.

8 Claims, 3 Drawing Sheets

METHOD FOR IDENTIFYING ACTIVE SUBSTANCES

BACKGROUND OF THE INVENTION

The invention relates to a method for identifying active substances and a device for executing the method.

In "Fourier-Transform Infrared Spectroscopic Studies on Avidin Secondary Structure and Complexation with Biotin and Biotin-Lipid Assemblies," Biophysical Journal Vol. 71 (1996), pp. 840–847, M. J. Swamy, T. Heimburg and D. Marsh describe efforts to explain the structure of complexes of the protein avidin with biotin and biotin-lipid through Fourier-transform infrared spectroscopy (FTIR). In this work, FTIR spectra of the avidin are first recorded in heavy water ($D_2O$). Then, avidin with biotin or biotin-lipid is mixed with buffered $D_2O$ as a solvent and stored for several hours at room temperature, which apparently should produce the highest yield of the resulting avidin complex. The FTIR spectra of the complex are recorded again. Differential spectra are formed from the spectra of the avidin and the spectra of the avidin complex. Because this work only focuses on the structure of the avidin complexes, no time-dependent spectra are recorded. In all instances, the described FTIR spectra reflect states of equilibrium. The vibrational spectra of bonded deuterium is recorded—shifted due to the higher mass—as opposed to the vibrational spectra of bonded, normal hydrogen.

Consequently, a comparatively thick cuvette (50 $\mu$m) can be used. The question of whether a chemical compound, such as a protein, may form at a coordination point with a specific ligand is of no consequence in this work, because the fact that a complex of avidin with biotin forms was already known.

FTIR studies for determining structures of protein complexes are also described by M. Gonzales, et al. in "Interaction of Biotin with Streptavidin," The Journal of Biological Chemistry, Vol. 272, No. 17 (1997), 11288–11294. The spectra were recorded with an $H_2O$ buffer as well as a $D_2O$ buffer; in the case of $H_2O$, the layer thickness was 6 $\mu$m, and 50 $\mu$m in the case of $D_2O$. The goal of the study was to ascertain the thermal stability of biotin and the biotin-streptavidin complex. The thermal denaturing was represented in chronologically consecutive spectra. In contrast, the formation of the complexes was not investigated with spectrometry.

In "Redox-linked conformational changes in proteins detected by a combination of infrared spectroscopy and protein electrochemistry—Evaluation of the technique with cytochrome c," Eur. J. Biochem. 187, 565–572 (1990), D. Moss, E. Nabedryk, J. Breton and W. Mantele report on an electrochemical reduction and a subsequent re-oxidation of the protein cytochrome c. Cytochrome c is provided in a layer thickness of 10 to 15 $\mu$m to preclude the IR absorption of water in the medium infrared range. The reduction and subsequent re-oxidation were proven with the aid of FTIR spectroscopy. Differential spectra of the reduced and re-oxidized state are shown. Because the cuvette only contained cytochrome c, no definitive statements could be made about the formation of protein complexes.

The publication by A. J. White, K. Drabble and C. W. Wharton: "A stopped-flow apparatus for infrared spectroscopy of aqueous solutions," Biochem. J. (1995) 306, 843–849 describes an apparatus for executing the so-called "stopped-flow" method, in which the reagents are sprayed into a cuvette with sprayers, and mixed. According to the authors, HPLC valves have proven unsuitable due to the necessary high pressure and the high viscosity of peptides. This apparatus was used to record FTIR spectra in the temporal range of 6.25 seconds to 966 seconds after the mixing of 12C=O- and 13C=O-cinnamoyl chymotrypsin with a deacylating agent in a $D_2O$ buffer; the optical layer thickness was 50 $\mu$m. Differential spectra were formed from the spectra of 12C=O- and 13C=O-cinnamoyl chymotrypsin. The "Conclusions" include the statement that it is not possible to create a "stopped-flow" IR transmission cuvette that permits the use of (non-deuterated) water, because the heavy absorption of water at 1640 cm$^-$ requires a layer thickness of 5 $\mu$m (the writings incorrectly state '5 mm').

Q. H. Gibson and L. Milnes provide a detailed description of the "stopped-flow" method in "Apparatus for Rapid and Sensitive Spectrophotometry," Biochem. J. (1964) 91, 161–171.

The large dead volume of the apparatuses due to the use of sprayers is a general drawback of the "stopped-flow" methods. Mass-screening methods, therefore, cannot be implemented with such apparatuses, notably because the microtitration plate provided with 96 depressions of 400 $\mu$l each is the standard model for automated methods; refer to J. R. Broach and J. Thorner: "High-throughput screening for drug discovery," Nature Vol. 384 Supp. Nov. 7, 1996, which offers an overview of mass-screening methods. With regard to ascertaining the bondability of a ligand to the receptor of a peptide, Broach and Thorner cite a method in which $Eu^{2+}$ at the ligand and allophycocyanin at the receptor are covalently bonded. Through the formation of a receptor-ligand complex, $Eu^{2+}$ closely approaches allophycocyanin, resulting in an energy transfer that can be detected as a fluorescence signal.

SUMMARY OF THE INVENTION

It is an object of the invention to develop a method for identifying active substances that permits the low-cost detection of the formation of complexes between reactants in the smallest-possible volume, flexibly and quickly and with reproducible results. The method is also intended to have the capability of being automated. It is a further object to provide a device for executing the method.

The above and further objects are accomplished according to the invention by the provision of a method comprising: mixing at least two reactants that form a reactant complex; recording an IR spectrum of individual reactants that have not yet been converted in the mixture at a first time; recording at least one further IR spectrum at a second time for detecting the reactant complex; forming a differential spectrum for the two IR spectra recorded at different times; and selecting the reactants whose differential spectrum has a band structure as active substances.

According to the invention, the active substances are identified through the investigation of the bondability of a reactant, such as a ligand, to at least one further reactant, such as a protein. The reactants produce a mixture from which an IR or FTIR spectrum is recorded at least at two different times. The ligand measurement can be effected in an aqueous solution, in which case the conventional use of deuterated solutions, such as deuterated water or a deuterated buffer, is not absolutely necessary. Depending on the viscosity and the physical-chemical properties of the reactants, the use of a different or further solvent may be indicated; a deuterated buffer or deuterated solvent can be omitted.

The mixture can be produced in accordance with the cited state of the technology. The use of high-pressure pumps (up to about 400 bar) and the loop valves known from HPLC technology is preferred, however.

The mixture should preferably be applied in a layer thickness of 1 to 25 μm, especially 8 to 15 μm. The mixture is advantageously produced on the way to and/or in an IR cuvette with a corresponding optical thickness.

Usually, one endeavors to produce a complete mixture from the organic compound and the reagent. Because most of the reactions of organic compounds take place slowly, the time required to produce an optimum mixture and record the first IR or FTIR spectrum is typically sufficiently short. If, however, the speed of reactions between the reactants is high, it may be advisable to record the first IR or FTIR spectrum with an incomplete mixture to prevent a substantial reaction conversion at this time.

In the recording of the first IR or FTIR spectrum, the reactants must still be at least partially unconverted, so the formation of the complex can be detected in the second or further IR or FTIR spectrum. Ideally, the reaction of the reactants should not have begun after the mixing. This is impossible for very rapid reactions due to the mixing prior to and/or on the way to the IR cuvette, so a portion of the reactants should have already reacted with one another. In the method of the invention, a partial reaction of the reactants is not problematic, provided that sufficient quantities of the reactants can react with one another and a measurement signal can be obtained. If the recording of the first IR or FTIR spectrum reveals that an inadequate portion of the reactants is present in unconverted form, only spectra no longer possessing sufficient differences can be recorded. The differential spectra in this case exhibit a zero line.

Preferably, a first FTIR spectrum is recorded immediately after the mixture is produced (time $t_0$). "Immediately" means that the spectrum is recorded as quickly as technically possible. Because the reaction speed is the highest immediately after the reactants have come into contact with one another, it is crucial for the rapidity and precision of the method that the reaction speed still be sufficiently high during the recording of the first spectrum, and that the primary portion of the reactants not react until afterward. Above all, in slower reactions, it is possible to wait for some time before recording the first spectrum, as long as the reaction speed of the reactants is sufficiently high to be measured. The first spectrum, however, is advantageously recorded within one to 1000 milliseconds after the reactants have been mixed.

In the method of the invention, differential spectra of two spectra that are recorded at arbitrary times are formed for identifying the active substance. The differential spectrum is preferably formed with the spectrum that is recorded immediately after the mixing of the reactants (measurement time $t_0$). A spectrum that has a large temporal spacing from this spectrum is preferably selected as the second spectrum. If more than two reactants are used in the measurement, the reaction is preferably started by the addition of the reactant that leads to the complex formation being investigated.

Substances whose pharmaceutical or phytopharmacy effect is presumed, and which are supposed to be investigated more closely, are used as reactants. Reactants can include, for example, potential medicines, potential herbicides, fungicides or insecticides that are capable of forming complexes.

The active substances in the method of the invention should preferably encompass those substances that exhibit a physiological effect in the plant, animal or human body, e.g., hormones, vitamins, enzymes, pharmaceuticals or pesticides. Active substances are reactants such as proteins, e.g., enzymes such as ECE or ACE, receptors, such as glutamate receptors, antibodies, protein inhibitors such as PAI, mediators, e.g., interferons such as gamma interferon, interleukins such as interleukin-2 or interleukin-6, transcription factors such as Sp1, regulator proteins, translocators or chaperones.

Low-molecular substances having an average molecular weight in a preferred molecular-weight range of 100 to 10,000 Daltons (=d), especially in a range of 100 to 1000 d, are also mentioned here. Low-molecular substances encompass organic chemical compounds that may contain, for example, substituted aliphatic or aromatic heterocyclene, aromatics, saturated or unsaturated aliphatics, amines, ketones, thioketones, alcohols, thiols, esters, amides, ethers, thioethers, nitriles, isonitriles, aldehydes or their derivatives.

Active substances that, by way of the release of a ligand which, as a reactant, ultimately forms a complex with the further reactant(s), can also be detected with the method of the invention.

In the method of the invention, the identification of complex formations between proteins is less preferable, because proteins cannot be administered orally, for example as active substances, and frequently cause allergic reactions. In the method of the invention, the complex formation between proteins, DNA or RNA and low-molecular substances is preferably investigated. In the method of the invention, at least one of the reactants can be a protein or a DNA; at least one further reactant should be a low-molecular substance. Interactions between long- and short-chain DNA or RNA can also be detected.

Primarily in the complex formation of and with proteins, but also in many other organic compounds, the medium IR range between 2500 and 12,500 nm is preferably used.

After a waiting period, a second IR or FTIR spectrum is recorded (time tn). The length of the waiting period (=x) depends on the reaction speed of the reaction partners. The length of the waiting period is between 1 ms and one day, preferably between 10 ms and 120 min, especially between 10 ms and 10 min. If one reactant is a protein, a waiting period in the range of aa5 to 30 s, e.g., 20 s, is suitable. Much shorter waiting periods, for example in the range of 10 to 100 ms, are required for investigating the avidin/biotin complex, for example. Waiting periods in the minute range should be implemented for the reaction of some antibodies and in the hybridization of DNA.

The reaction conversion that has taken place to this point is documented in the second IR or FTIR spectrum. This reaction conversion can be represented through the formation of a differential spectrum between the first spectrum, for example at $t_0$, and the second spectrum at $t_n$. The differential spectrum is formed according to $\Delta A_v = {}^{10}\log(I_{1v}/I_{2v})$, where $I_{1v}$ and $I_{2v}$ are the measured intensities at the frequency v in the first and second spectrum, respectively.

If the differential spectrum essentially comprises a straight line, no reaction has occurred, because in this case the concentration of the reaction partners does not change. A bonding of the reactants is therefore manifested in a differential spectrum having a band structure.

In the method of the invention, complexes include all covalently or non-covalently bonded reactants or their components. Non-covalent bonds include bonds formed by van-der-Waals forces, a hydrogen-bridge bond or ionic bonds. According to the invention, non-covalently bonded reactants or their components are preferred.

A significant merit of the method according to the invention is that the method can be automated, so the reactant complexes can be formed quickly, either consecutively or in parallel. So-called mass-screening methods are particularly significant for the development of new medications. In this process, a protein that is associated with the manifestation of an illness, for example, is identified. The object is to find a suitable medication that inhibits this so-called target protein. The target protein can be obtained from the corresponding biological material in large quantities and with high purity. Numerous reagencies whose pharmaceutical effectiveness is presumed are tested to determine whether they possess the desired inhibitory effect. The number of reagencies to be tested is generally very large, even a five-, six- or seven-digit number, so the use of a fast, automatic screening method is of critical economic significance.

This object can be accomplished by the method according to the invention. The high scanning speeds of modern FTIR spectrometers and the short time required for executing the method establish the prerequisites for testing a large number of reagencies. A further notable advantage of the method is that the conventional, standard microtitration plates can be used without problems. Because the trend is toward even smaller microtitration plates having 384 or even 864 holes, which have a lower volume of about 100 $\mu$l or about 50 $\mu$l, the small sample quantity required for the method and device of the invention is especially significant. Further important advantages of the method, and the reasons that the method is suitable for mass-screening methods, are that no deuterated water need be used, and the device can be used without any structural modifications for numerous studies.

BRIEF DESCRIPTION OF THE DRAWINGS

An embodiment of the device for executing the method of the invention is described in conjunction with the figures, which show in.

DETAILED DESCRIPTION OF THE INVENTION

Figure 1:
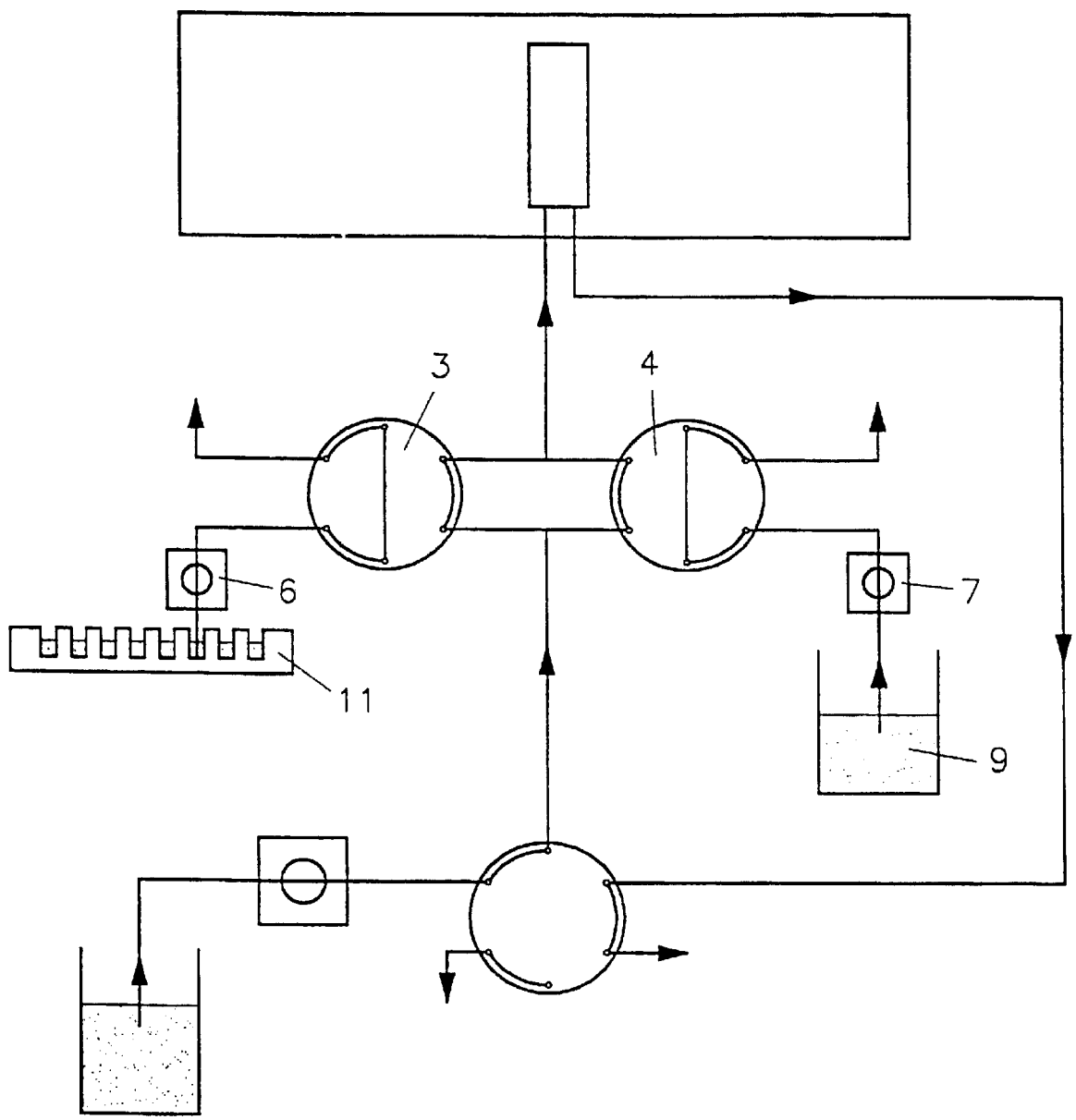
FIG. 1 the embodiment of the device in a first operating state.

FIG. 1 shows the device in a first operating state, in which the valves 3 and 4 are filled with a test substance or a target protein. The test substances are placed on an xyz positioning table in a standard microtitration plate 11, and the target protein is placed in a reservoir 9. The valves 3 and 4 are turning valves (by the Valco company) known from HPLC technology; in the illustrated position, they are switched such that the two low-pressure pumps 6 and 7 can fill them with a test substance from the standard microtitration plate 11 or the target protein from the reservoir 9. In both cases, any excess is conducted into the sewer system (not shown).

Figure 2:
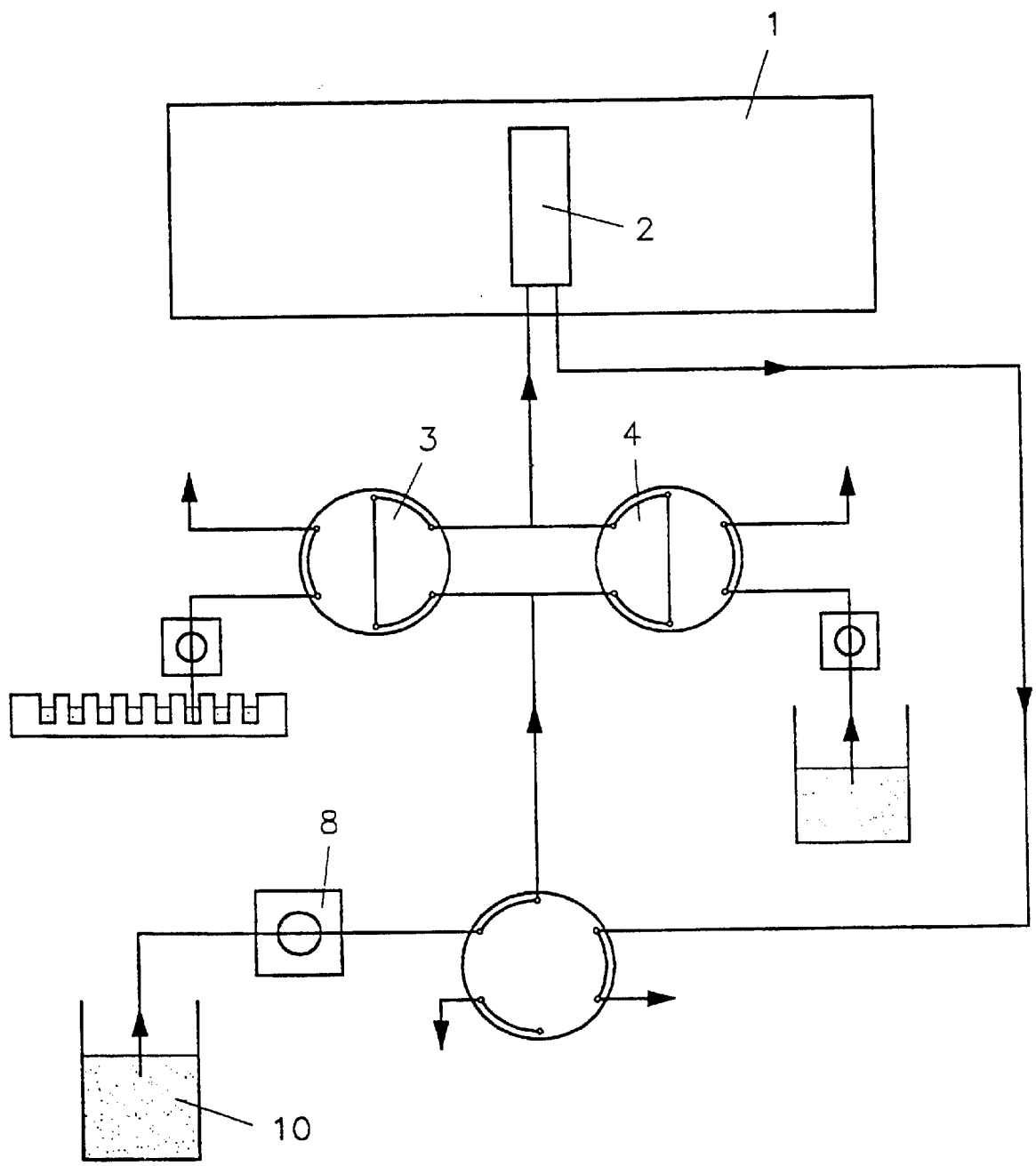
FIG. 2 the embodiment of the device in a second operating state.

In the operating state illustrated in FIG. 2, the valves 3 and 4 are reversed. The test substance and the target protein are mixed with the aid of the high-pressure pump 8, which is connected to a reservoir 10 for distilled water, and transported into the IR cuvette 2 in the FTIR spectral photometer 1.

Figure 3:
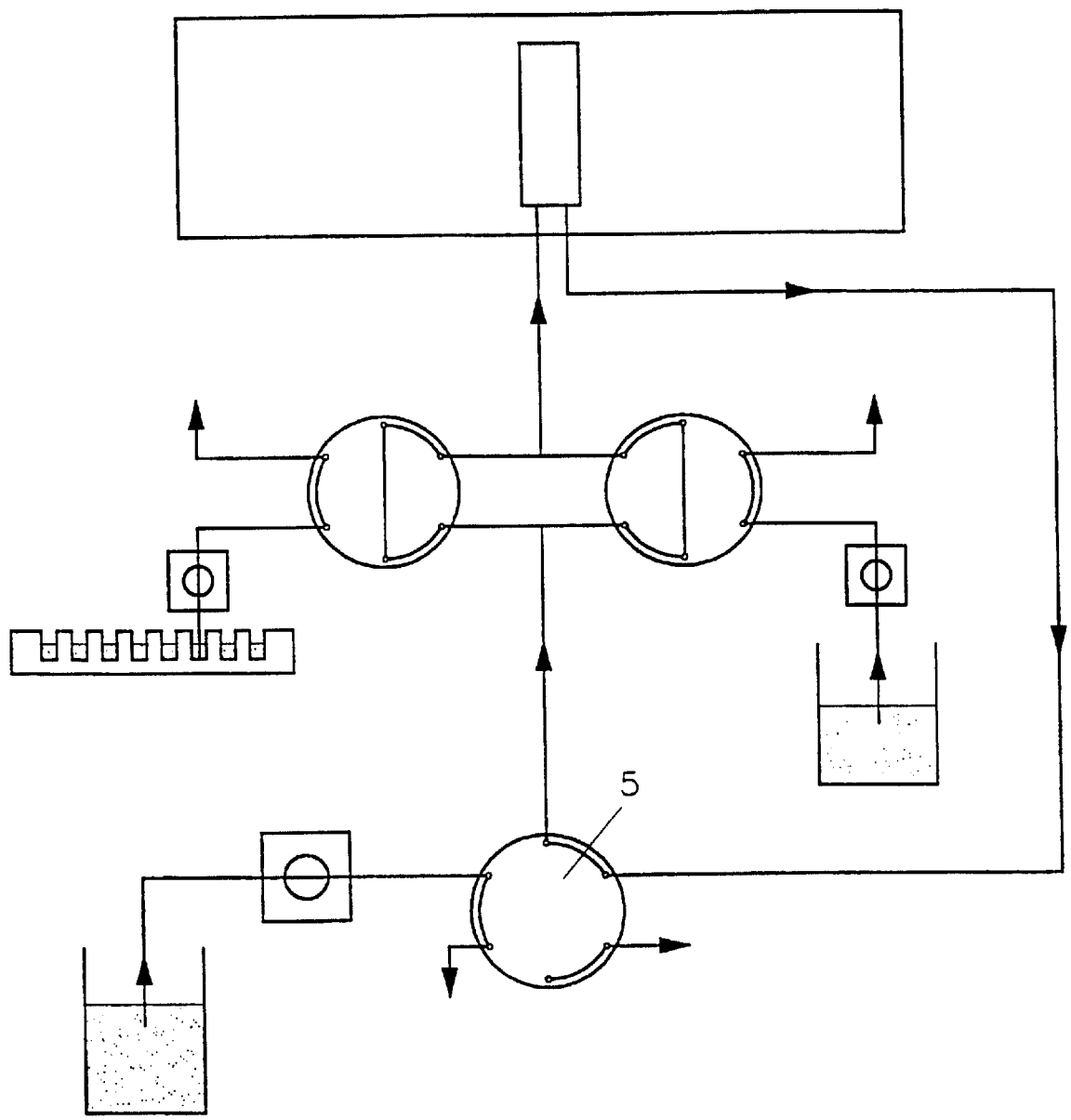
FIG. 3 the embodiment of the device in a third operating state.

FIG. 3 illustrates the operating state in which the first FTIR spectrum ($t_0$) and, after a waiting period, the second FTIR spectrum ($t_n$), are recorded. The valve 5 is reversed here, so the test substance and the target protein are isolated in a closed line system.

After the spectra are recorded, the measurement cell is rinsed with distilled water before the cycle begins again.

The device is essentially constructed from HPLC components. The high-pressure pump 8 is an HPLC pump (by the Alltech company), which is well-suited for continuous high-pressure operation. All fluid lines and connections comprise HPLC components that can be loaded up to 400 bar. To reduce wear and tear on the HPLC pump, only distilled water is pumped. The selected arrangement of the HPLC turning valves 3, 4 and 5 assures the additional advantages of efficient cleaning of the system, and a reduced consumption of sample material, which are significant for mass screening. With the aid of the turning valve 5, the high-pressure pump 8 diverts, rather than stops, the flow of distilled water from the reservoir 10, so the flow through the IR cuvette can be stopped. This process reduces wear and tear on the pump, resulting in a faster response time. Moreover, this short-circuits the intake and discharge lines of the IR cuvette, which quickly compensates the overpressure and eliminates changes in layer thickness due to bulging of the IR cuvette.

The device illustrated in the figures can be used to achieve throughput speeds of up to 40 ml/min, which correspond to an exchange of the contents of the IR cuvette within 15 ms. A pressure of up to about 150 bar is recorded. The valve 5 diverts the fluid flow in 20 ms. It suffices to use 100 $\mu$l each of the target protein and the test substance for recording the FTIR spectra; this amount can be reduced further by a factor of 3 to 5 through the optimization of the sample requirement.

What is claimed is:

1. A method for identifying active substances, comprising:

mixing at least two reactants that form a reactant complex;

recording an IR spectrum of individual reactants that have not yet been converted in the mixture at a first time;

recording at least one further IR spectrum at a second time for detecting the reactant complex;

forming a differential spectrum for the two IR spectra recorded at different times; and selecting the reactants whose differential spectrum has a band structure as active substances.

2. The method according to claim 1, further comprising:

selecting a time immediately following the mixing of the reactants as the first time.

3. The method according to claim 1, wherein at least one of the reactants is a low-molecular compound.

4. The method according to claim 1, wherein at least one of the reactants is a protein.

5. The method according to claim 1, wherein at least one of the reactants is a DNA molecule.

6. The method according to claim 1, wherein there is a waiting period in a range of one millisecond to one day between the first and second times.

7. The method according to claim 1, including placing the reactants in a microtitration plate and executing the method successively or in parallel with a plurality of reactants.

8. The method according to claim 1, including measuring the IR spectra in a layer thickness of 1 to 25 $\mu$m.

* * * * *